US00PP32219P2

(12) United States Plant Patent
NeSmith

(10) Patent No.: US PP32,219 P2
(45) Date of Patent: Sep. 22, 2020

(54) SOUTHERN HIGHBUSH BLUEBERRY PLANT NAMED 'TH-1008'

(50) Latin Name: *Vaccinium corymbosum*
Varietal Denomination: TH-1008

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc, Athens, GA (US)

( * ) Notice: Subject to any disclaimer, the term of this patent is extended or adjusted under 35 U.S.C. 154(b) by 0 days.

(21) Appl. No.: 16/602,611

(22) Filed: Nov. 7, 2019

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Klarquist Sparkman, LLP

(57) ABSTRACT

The new variety 'TH-1008' is provided. The new and distinct variety flowers in early March in south Georgia, requiring frost protection for acceptable yields. The fruit of the new variety 'TH-1008' are ripen in early May in south Georgia and are very large, firm, and have good flavor. The new variety 'TH-1008' is compact with an estimated chilling requirement of about 200 to 300 hours at or below approximately 7° C. The asexually reproduced variety is reliably propagated vegetatively.

7 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-1008' is a southern highbush blueberry plant that is a *Vaccinium corymbosum.*

Variety denomination: The new southern highbush blueberry plant claimed is of the variety denominated 'TH-1008'.

BACKGROUND OF THE INVENTION

The present invention relates to the discovery of a new and distinct cultivar of southern highbush blueberry plant botanically known as a *Vaccinium corymbosum* and herein referred to as 'TH-1008', as herein described and illustrated.

The new blueberry plant variety 'TH-1008' was selected in Griffin, Ga. in 2006. The new variety 'TH-1008' has a long flowering and harvest season, flowering in early March and ripening in early May in southern Georgia. The fruit of the new variety 'TH-1008' are high quality but the yield is dependent on frost protection. The new variety 'TH-1008' is compact and has an estimated chilling requirement of about 200-300 hours at or below 7° C.

Pedigree and history: 'TH-1008' was selected in 2006 at a plant experiment station in Griffin, Ga., originating from a cross of 'TH-687' (female parent, non-patented breeding selection) X 'Emerald' (male parent, U.S. Plant Pat. No. 12,165) made in 2003 by D. Scott NeSmith. The selection has been asexually propagated by vegetative stem cuttings and tested in plantings at blueberry research farms in Alapaha, Ga. since 2011.

SUMMARY OF THE INVENTION

The new blueberry plant variety 'TH-1008' has not been observed under all possible environmental conditions. The phenotype may vary somewhat with variations in environment and cultural practices such as temperature and light intensity without, however, any variance in genotype.

The following traits have been repeatedly observed in plants of the 'TH-1008' variety growing at Alapaha, Ga. and are determined to be the unique characteristics of the new blueberry plant variety 'TH-1008':

1. Compact;
2. Long flower and ripening period;
3. Early ripening; and
4. Produces large, light-blue berries.

The new variety 'TH-1008' can be compared to the early ripening southern highbush blueberry varieties 'Suziblue' (U.S. Plant Pat. No. 21,167) and 'Rebel' (U.S. Plant Pat. No. 18,138).

Comparison: The 'TH-1008' variety is early season and begins ripening after the early varieties 'Suziblue' and 'Rebel' in south Georgia. 'TH-1008' has large, very firm berries with good flavor as compared to 'Suziblue' and 'Rebel' at Alapaha, Ga. (Table 1).

TABLE 1

3-year average ratings of some fruit and plant characteristics of 'TH-1008' and standard cultivars 'Suziblue' and 'Rebel' from 2014 thru 2016 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2011.

| Berry and plant attributes | Alapaha location | | |
|---|---|---|---|
| | 'Suziblue' | 'Rebel' | 'TH-1008' |
| Berry size | 7.9 | 7.3 | 8.8 |
| Berry scar | 7.3 | 7.2 | 7.5 |
| Berry color | 7.0 | 7.3 | 7.9 |
| Berry firmness | 7.5 | 7.3 | 7.6 |
| Berry flavor | 7.3 | 6.3 | 7.6 |
| Cropping | 6.9 | 5.3 | 4.5 |
| Plant vigor | 8.1 | 7.1 | 8.1 |
| Date of 50% flowering | Feb. 28 | Feb. 28 | Mar. 1 |
| Date of 50% ripening | May 8 | May 1 | May 10 |
| Fruit development period (days) | 68 | 63 | 70 |

BRIEF DESCRIPTION OF THE FIGURES

The accompanying photographic illustrations show typical specimens in full color of the foliage, flowering, and fruit of the new variety 'TH-1008'. The colors are as nearly true as is reasonably possible in a color representation of this type.

BOTANICAL DESCRIPTION

Figure 1:
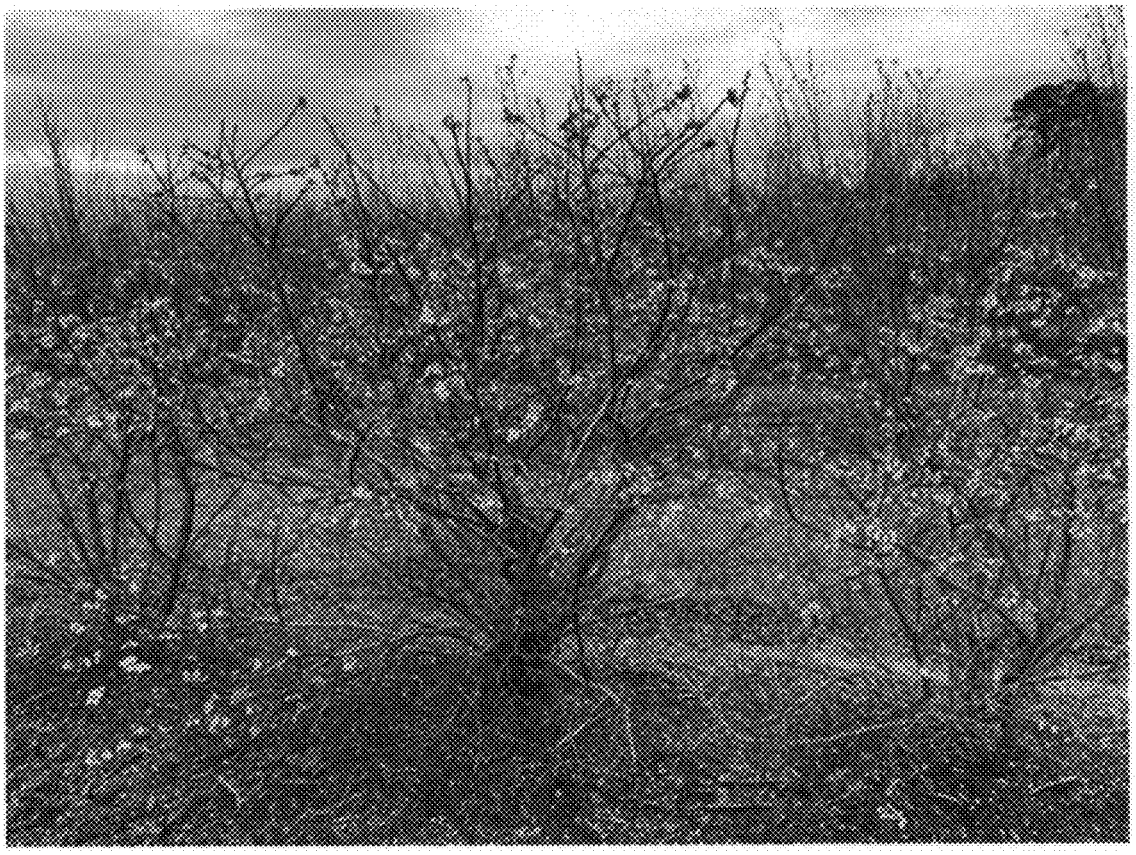
FIG. 1 is a photograph of plants of the new variety 'TH-1008' during flowering in Alapaha, Ga.
Figure 2:
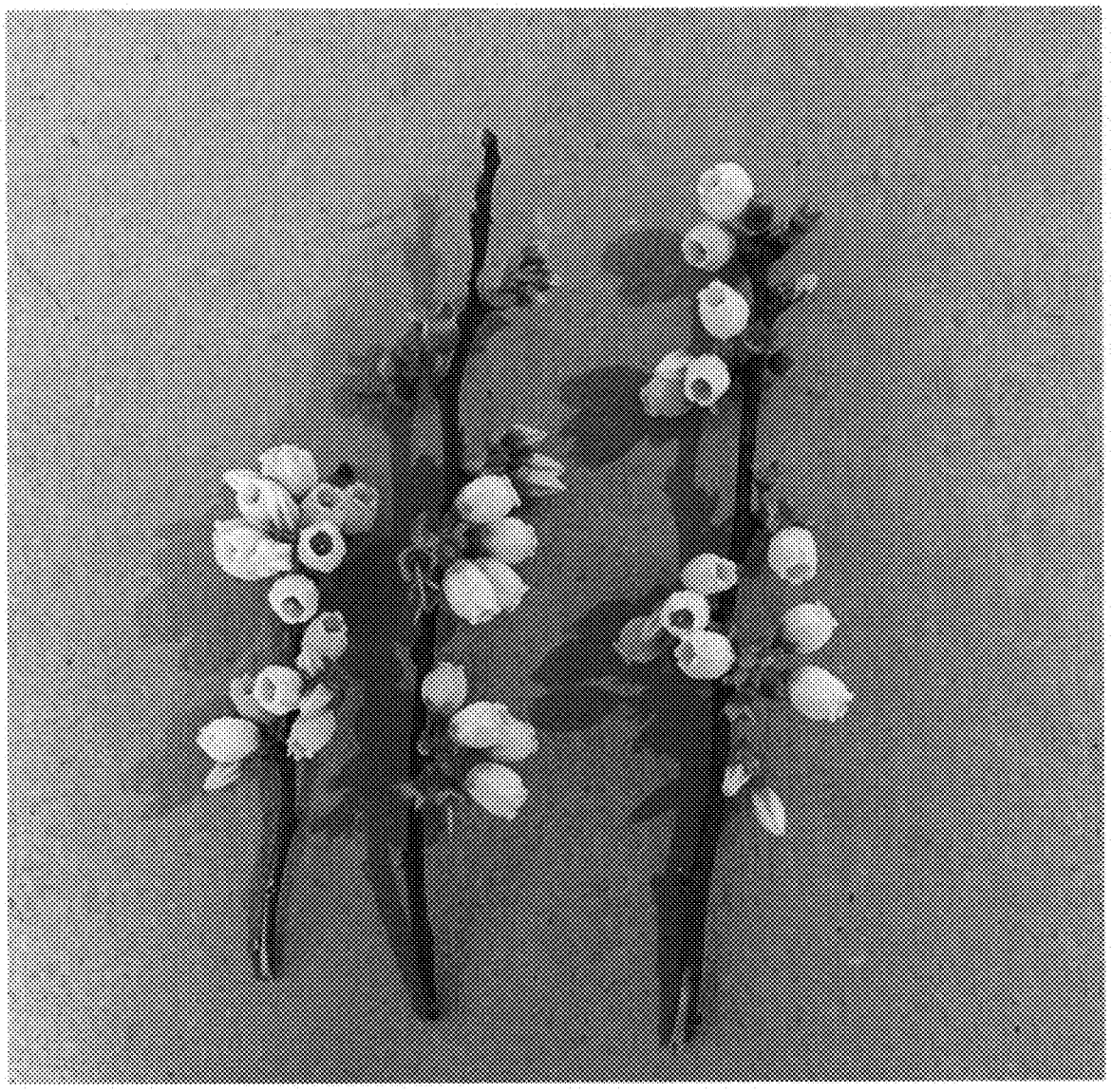
FIG. 2 is a close up photograph of flowers of the new variety 'TH-1008'.
Figure 3:
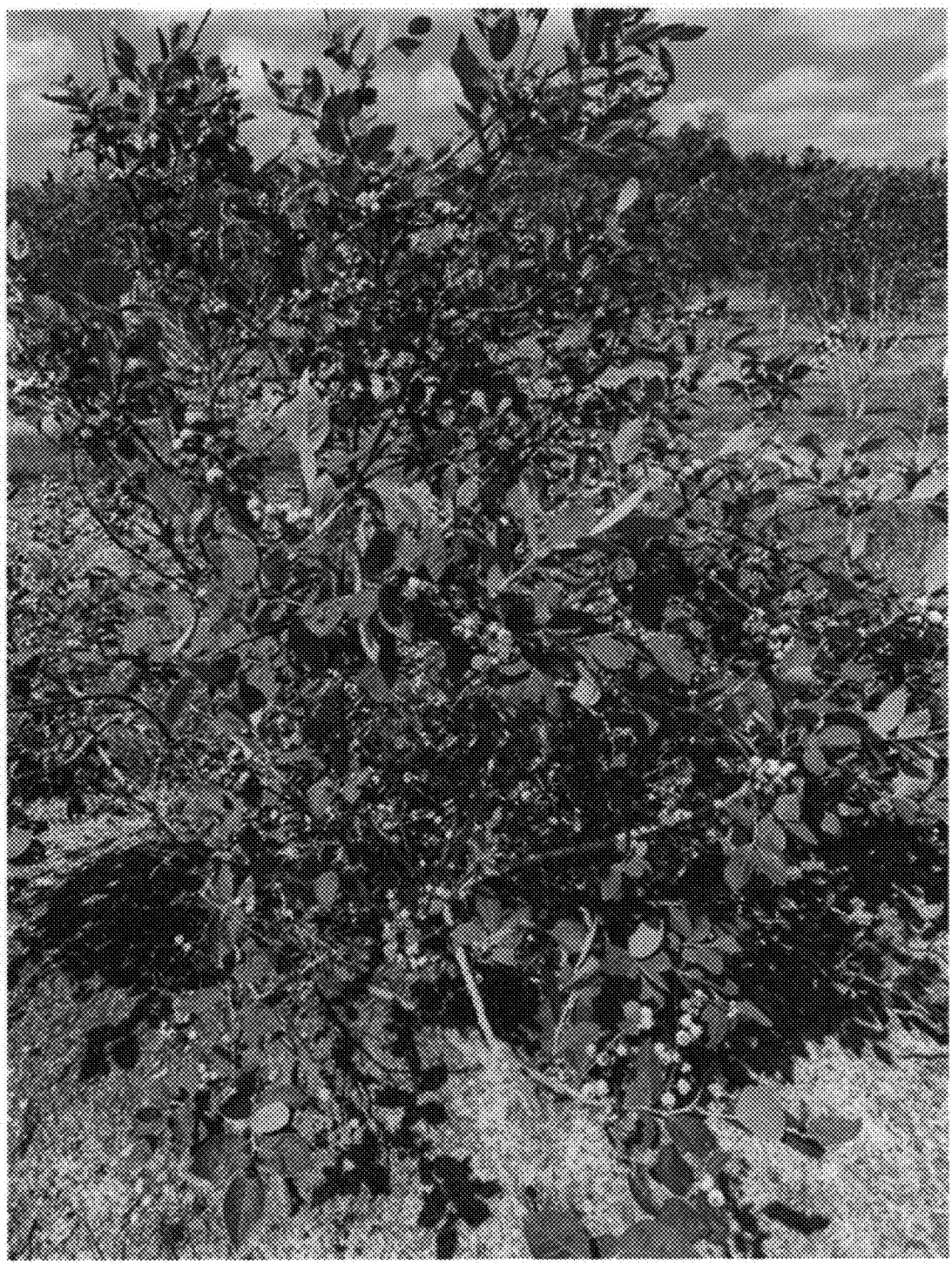
FIG. 3 is a photograph of a plant of the new variety 'TH-1008' during fruit ripening in Alapaha, Ga.
Figure 4:
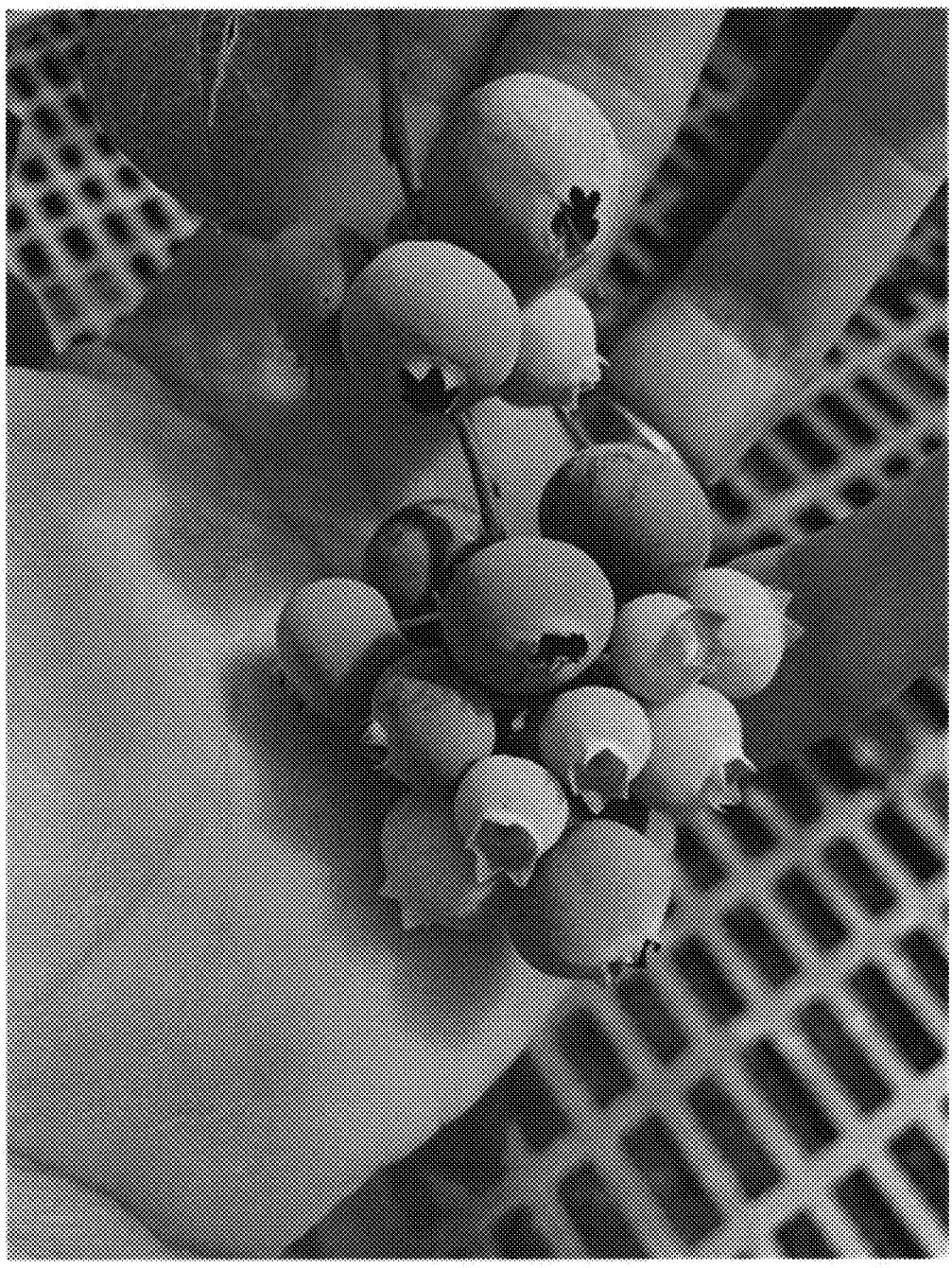
FIG. 4 is a close up photograph of fruit clusters of the new variety 'TH-1008'.
Figure 5:
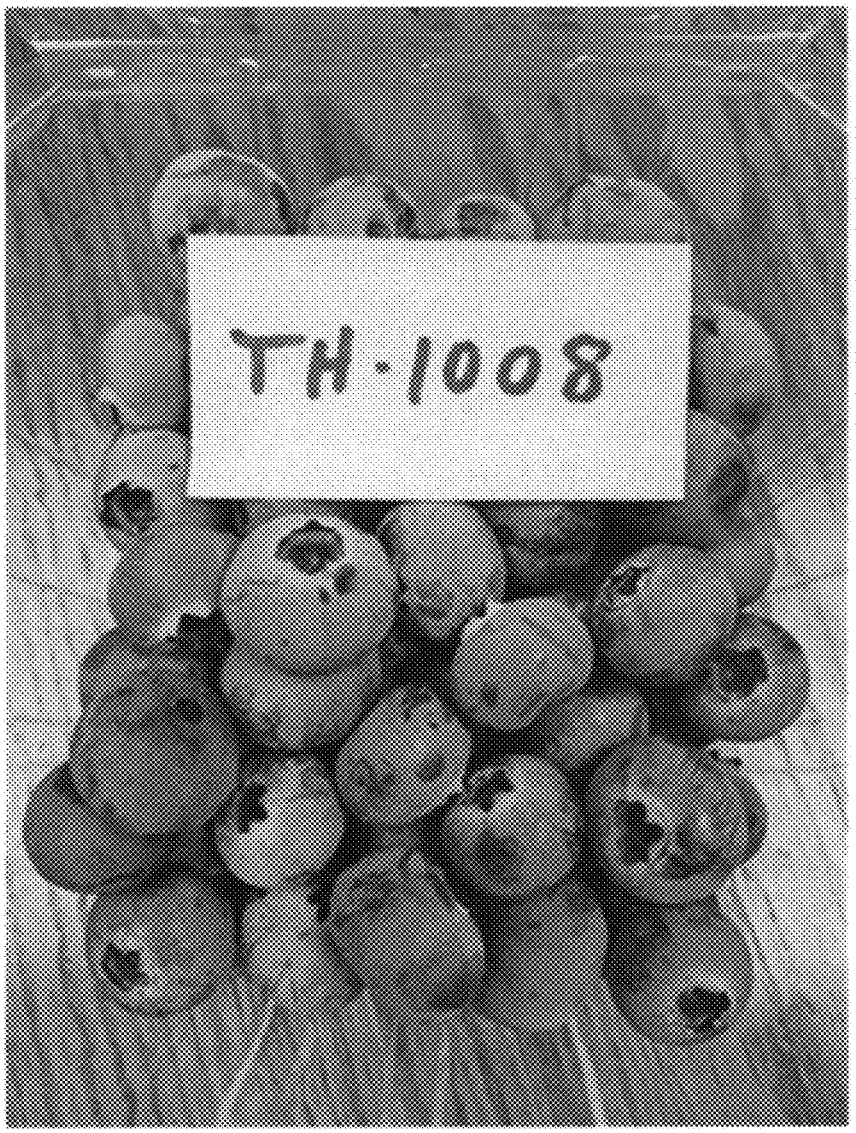
FIGS. 5, 6 and 7 are photographs of harvested fruit of the new variety 'TH-1008'.
Figure 6:
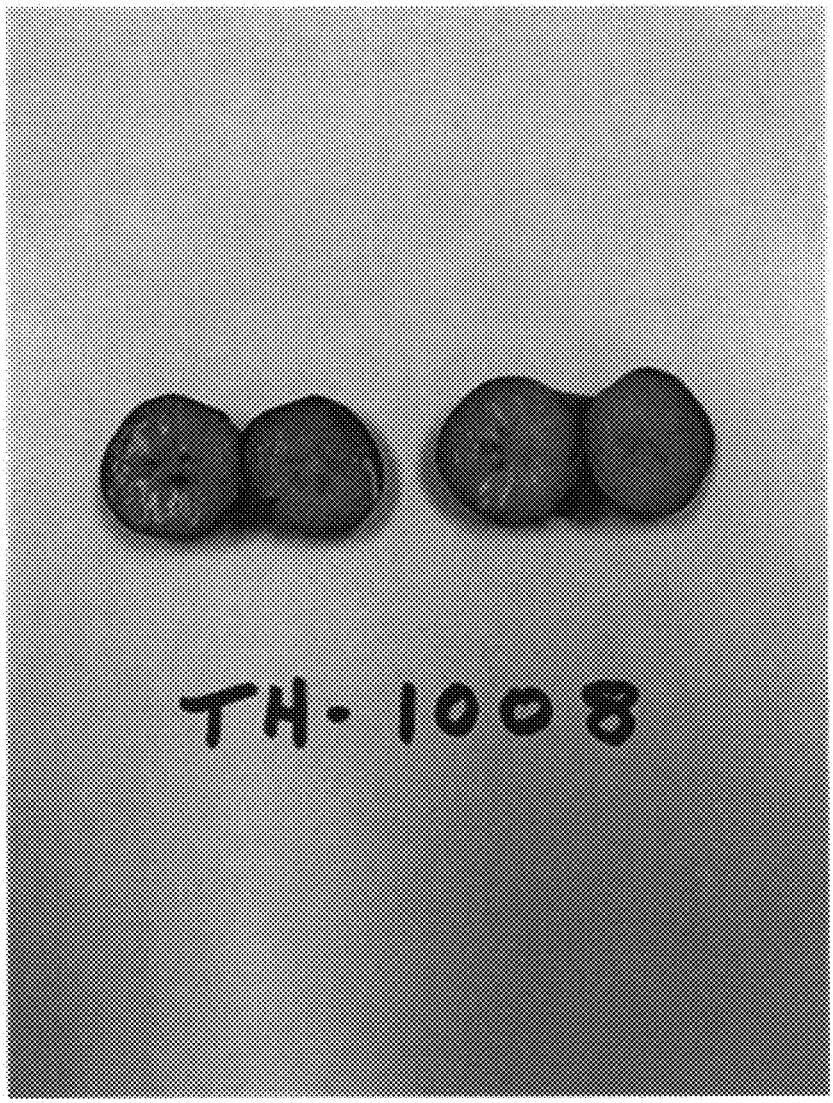
Figure 7:
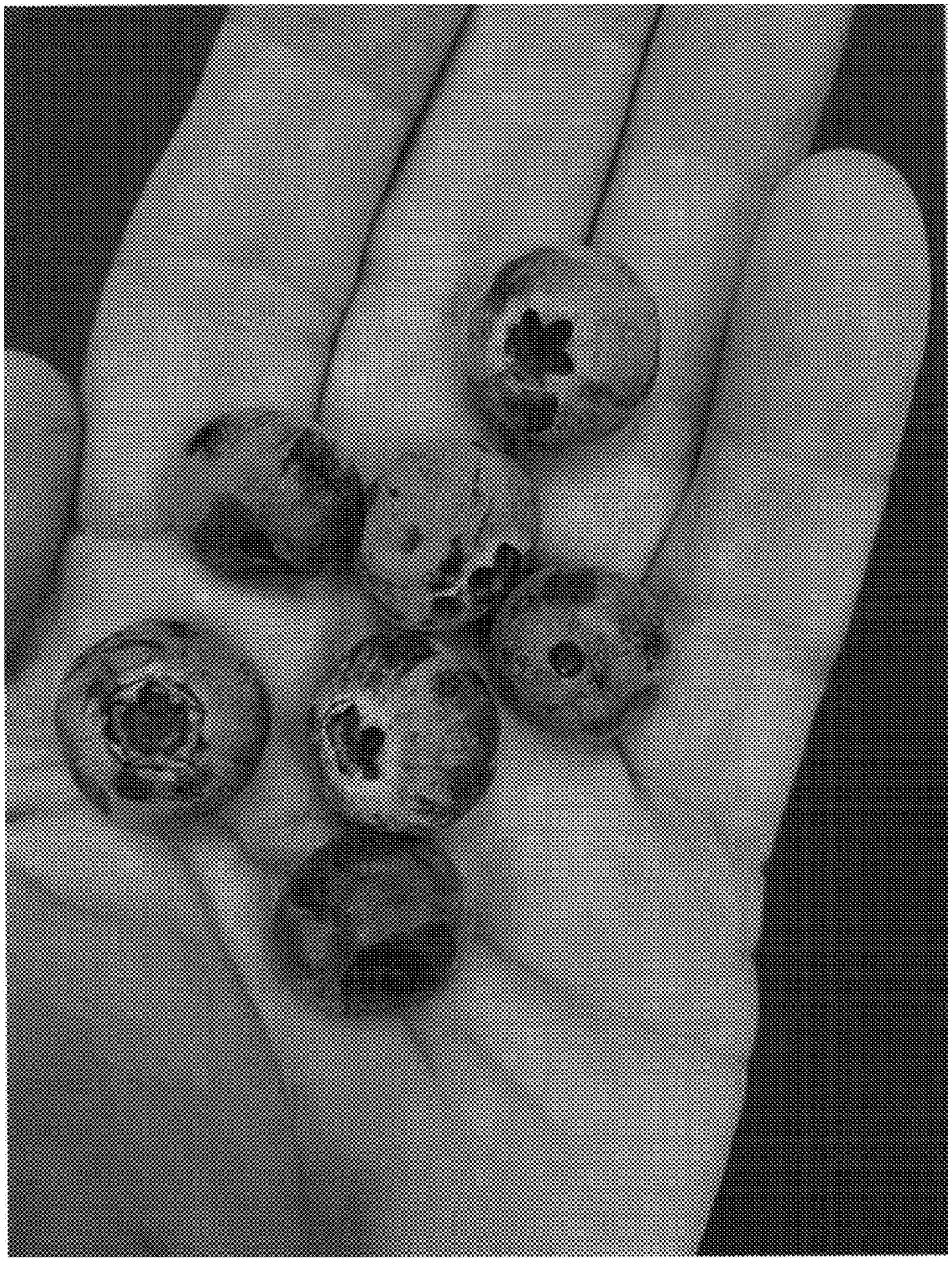

Throughout this specification, color names beginning with a small letter signify that the name of that color, as used in common speech, is aptly descriptive. Color names beginning with a capital letter designate values based upon The R.H.S. Colour Chart, 5$^{th}$ edition published in 2007 by The Royal Horticultural Society, London, England.

The following is a detailed description of the botanical and pomological characteristics of the new variety 'TH-1008'. Where dimensions, sizes, colors, and other characteristics are given, it is to be understood that such characteristics are approximations and averages set forth as accurately as practicable. The descriptions reported herein are largely from four to six year old specimen plants grown in Alapaha, Ga. with supplemental irrigation.

Plant:

*Size.*—1.2 to 1.4 m tall by 3 years. Plants grown under highly productive soil and fertility conditions have exceeded 1.5 m tall in 4 years. The plant crown, or base, is narrow, typically 10 to 15 cm in diameter. Upper portion of plant canopy reaches 1.2 to 1.5 m in diameter by 3 to 4 years.

*Growth habit.*—Compact and semi-spreading, with 2 to 4 main canes arising from the crown, and multiple branching of shoots from those canes 10 to 15 cm above ground.

*Growth.*—Compact and moderately vigorous.

*Productivity.*—Medium to high crop yield, averaging 5 to 9 lbs of fruit per plant each year for plants 4 years and older grown under well fertilized and irrigated field conditions. Frost protection is required to reach yield potential due to early flowering.

*Hardiness.*—Has been grown in Alapaha, Ga. and Griffin, Ga., USDA hardiness zone 8a; similar to other early ripening southern highbush varieties such as 'Suziblue' and 'Rebel'.

*Chilling requirement.*—Very low to mid chill, requiring only 200 to 300 hours, more or less, of temperatures at or below 7° C. to induce normal leafing and flowering during the spring under conventional dormant production systems. The chill requirement is more than the male parent 'Emerald' (100 to 150 hours of chilling required), but less than the female parent 'TH-687' (400 to 500 hours of chilling required).

*Leafing.*—Plants tend to break sufficient leaf buds simultaneously with, or shortly after, anthesis.

*Fruiting wood.*—Moderate number of twigs 10 to 15 cm in length, with internode lengths of 15 to 25 mm common.

*Canes.*—Diameter: Main cane base diameter 15 to 25 mm, two year old cane diameter 10 to 15 mm, current season wood diameter 3 to 5 mm. Color: Main cane color most near Brown N200D, two year old cane transitions from Yellow Green 145B to Greyed Orange 165A. Yellow Green 145B in current season wood.

*Disease and pest resistance.*—No exceptional disease and pest resistance or susceptibility observed. Typical for early season southern highbush 'Suziblue' and 'Rebel' cultivars.

Foliage:

*Leaf color.*—Healthy mature leaves. Top side: Green 137B. Under side: Green N138C.

*Leaf arrangement.*—Alternate, simple.

*Leaf shape.*—Elliptic.

*Leaf surface.*—Glaucous.

*Leaf margins.*—Entire and smooth.

*Leaf venation.*—Arcuate, slightly to moderately reticulated.

*Leaf apices.*—Broadly acute.

*Leaf bases.*—Acute.

*Leaf dimensions.*—Length: 60.0 to 75.0 mm. Width: 35.0 to 40.0 mm.

*Petioles.*—Length: 3.5 to 5 mm. Width: 1.5 to 2.2 mm. Color: Yellow-Green 145C.

Flowers:

*Date of* 50% *anthesis.*—March 1 in southeast Georgia (3 year average).

*Flower shape.*—Urceolate.

*Flower bud number.*—High, averaging 4 to 6 buds per fruiting shoot.

*Flowers per cluster.*—5 to 9 common.

*Flower fragrance.*—Slight cut flower fragrance.

*Corolla.*—Color: White NN 155B to White NN 155C (open flower). Length: 8.0 to 10.0 mm. Width: 7.0 to 8.0 mm. Aperture width: 3.0 to 4.0 mm.

*Flower peduncle*.—Length: 7.0 to 8.0 mm. Color: Green 138D.

*Flower pedicle*.—Length: 3.0 to 5.0 mm. Color: Green 138D.

*Calyx* (*with sepals*).—Diameter: 7.0 to 9.0 mm. Color: Green 138D.

*Stamen*.—Length: 6.0 to 7.0 mm. Number per flower: 10. Filament color: Green White 157B.

*Style*.—Length: 9.0 to 10.0 mm. Color: Yellow Green 145B to 145C.

*Pistil*.—Length: 10.0 to 11.0 mm. Ovary color (exterior): Green 138C.

*Anther*.—Length: 4.0 to 5.0 mm. Number: 10. Color: Greyed-Orange 166C.

*Pollen*.—Abundance: Low to medium. Color: White NN 155A.

*Self-compatibility*.—The cultivar has a moderate degree of self-compatibility.

Fruit:

*Date of* 50% *maturity*.—May 10 in southeast Georgia (3 year average).

*Fruit development period*.—70 days.

*Berry color*.—With wax: Blue 100D. With wax removed: Black 203C.

*Berry surface wax abundance*.—High to very high.

*Berry flesh color*.—Green White 157A.

*Berry weight*.—First harvest: 3.1 to 3.6 g. Second harvest: 1.9 to 2.4 g.

*Berry size*.—Height from calyx to scar: 14.0 to 17.0 mm. Diameter: 16.0 to 20.0 mm.

*Berry shape*.—Semi-spherical to disk shape.

*Fruit stem scar*.—Small to medium, dry, with no tearing upon harvest.

*Calyx*.—Depth shallow, 2.0 to 3.0 nun; width 5.0 to 7.0 mm; sepals usually present, semi-erect or inward when present, 1.0 to 2.0 mm.

*Berry firmness*.—Good to very good.

*Berry flavor and texture*.—Semi-sweet, mildly acidic flavor; smooth texture.

*Storage quality*.—Very good.

*Suitability for mechanical harvesting*.—Not likely suitable.

*Uses*.—Primarily to be used as fresh fruit for shipping and processing markets.

Seed:

*Seed abundance in fruit*.—Low to medium, with 5 to 10 fully developed seeds per berry.

*Seed color*.—Greyed-Orange 165B.

*Seed dry weight*.—72.0 mg per 100 seed.

*Seed size*.—1.8 to 2.1 mm long.

What is claimed is:

1. A new and distinct variety of southern highbush blueberry plant named 'TH-1008', as illustrated and described herein.

* * * * *